United States Patent [19]

Tennison et al.

[11] Patent Number: 5,622,997

[45] Date of Patent: Apr. 22, 1997

[54] PROCESS FOR PREPARING A MOLDED ION EXCHANGE RESIN STRUCTURE

[75] Inventors: Stephen R. Tennison; Richard H. Weatherhead, both of Surrey, England

[73] Assignees: BP Chemicals Limited; The British Petroleum Co., p.l.c., London, England

[21] Appl. No.: 469,232

[22] Filed: Jun. 6, 1995

[30] Foreign Application Priority Data

Jul. 4, 1994 [GB] United Kingdom .................... 9413408

[51] Int. Cl.$^6$ .......................... C08F 236/00; C08F 279/00
[52] U.S. Cl. ................... 521/33; 521/29; 521/31; 521/32; 525/344
[58] Field of Search ................... 521/29, 31, 33, 521/32

[56] References Cited

U.S. PATENT DOCUMENTS

| | | | |
|---|---|---|---|
| 3,965,039 | 6/1976 | Chaplits | 568/899 |
| 3,970,534 | 7/1976 | Fujiwara | 521/33 |
| 4,242,530 | 12/1980 | Smith, Jr. . | |
| 4,302,356 | 11/1981 | Smith, Jr. . | |
| 4,339,548 | 7/1982 | Miyahara . | |
| 4,695,592 | 9/1987 | Itoh | 521/54 |
| 4,794,088 | 12/1988 | Miyaki | 436/161 |
| 5,057,468 | 10/1991 | Adams . | |
| 5,189,001 | 2/1993 | Johnson . | |
| 5,235,102 | 8/1993 | Palmer et al. . | |
| 5,244,929 | 9/1993 | Gottlieb et al. | 521/29 |

FOREIGN PATENT DOCUMENTS

| | | |
|---|---|---|
| 105885 | 3/1987 | European Pat. Off. . |
| 466954 | 1/1992 | European Pat. Off. . |
| 75-29266W/18 | 10/1995 | Germany . |
| 56-076408 | 6/1981 | Japan . |
| 93-070339/09 | 1/1993 | Japan . |
| 7761246CA | 1/1970 | Russian Federation . |
| 80-42798C/24 | 10/1979 | Russian Federation . |
| 79-76614B/42 | 7/1976 | U.S.S.R. . |
| 1443009 | 7/1976 | United Kingdom . |

OTHER PUBLICATIONS

"Recovery of Dilute Acetic Acid by Esterification in a Packed Chemorectification Column"; *Ind. Eng. Chem. Process Des. Dev.*; R. Neumann and Y. Sasson; vol. 23, pp. 654–659; ©1984.

"Design and Industrial Application of Polymeric Acid Catalysts"; *Syntheses and Separations Using Functional Polymers*; H. Widdecke; pp. 149–179; ©1988.

*Primary Examiner*—Fred Zitomer
*Attorney, Agent, or Firm*—Fay, Sharpe, Beall, Fagan, Minnich & McKee

[57] ABSTRACT

A moulded ion exchange resin structure suitable for use in reactive distillation is prepared by compressing particles of an ion exchange resin precursor having chemically reactive functional groups on their surfaces, into a preform having a predetermined shape, subsequently chemically bonding the particles together by reaction of the functional groups for example by acid-catalysed condensation and converting the precursor to an ion exchange resin, for example by sulphonation.

9 Claims, No Drawings

PROCESS FOR PREPARING A MOLDED ION EXCHANGE RESIN STRUCTURE

The present invention relates to a process for preparing a moulded ion exchange resin structure and in particular a structure suitable for use in a reactive distillation process.

Reactive distillation allows displacement of equilibria under reaction conditions which improves yields and also improves reaction selectivities by rapid removal of products from a reaction zone.

Heterogeneous catalysts may not be suitable for use in reactive distillation because the catalysts may not be in a form suitable for packing directly into a distillation column without causing severe pressure drops. Thus, H. Widdecke ("Syntheses and Separations using Functional Polymers" Edited by D. C. Sherrington and P. Hodge, 1988 John Wiley & Sons Ltd) in discussing the industrial application of polymeric acid catalysts states that in the case of a reversible reaction, the equilibrium may be shifted by carrying out the reaction and distillation in the same column. As the maximum bead size available by suspension polymerisation is about 1.5 mm, they (the ion exchange resin beads) are not well suited for this operation.

European patent 105,885-B describes a reactive distillation process for the production of highly pure methyl acetate in which Amberlite 200 (TM), an acidic cation exchange resin, may be used as a catalyst for the process. However, the use of a cation exchange resin requiring packed sections in the column is said to involve rather complex reactor designs.

Neumann, R and Sasson, Y attempted to overcome the problems of using solid catalysts in a chemorectification column in Ind. Eng. Chem. Process Des. Dev. 1984, 23, 654–659 in which they described the use of a packed column filled with a combination of acidic organic polymer catalyst and Raschig rings.

U.S. Pat. No. 4,302,356 states that resin beads in a conventional fixed bed form too compact a mass for an upward flowing vapour and a downward flowing liquid. However, by placing the resin beads into a plurality of pockets in a cloth belt, which is supported in a distillation column reactor by open mesh knitted stainless steel wire by twisting the two together, allows the requisite flows, prevents loss of catalyst, allows for the normal swelling of the beads and prevents the breakage of the beads through mechanical attrition.

U.S. Pat. No. 5,057,468 relates to catalytic distillation structures comprising small rigid closed containers into which may be loaded a catalyst, for example, an ion exchange resin. Openings in the containers allow vapour and liquid passage into and out of the containers. A multitude of catalyst containers may be placed into a distillation column with the surfaces of the containers providing the necessary vapour/liquid contact surfaces for the distillation and the rigidity of the containers providing for spacing the structures and the necessary free space for distillation. However, these methods of utilising ion exchange resins in reactive distillation processes are not entirely satisfactory.

In U.S. Pat. No. 4,339,548 it is stated that especially where ion-exchange resins are used for catalyst, resins having particle diameters considerably greater than those prevalent today are advantageous for packing columns. U.S. Pat. No. 4,339,548 describes a method for producing ion exchange materials of large dimensions, including large resin grains and cemented resin structures which method comprises cohering ordinary minute cation exchange and anion-exchange resin particles into coarse cementitious ion-exchange resin grains or structures by the use of an adhesive polymeric composition possessing a hydrophilic group. Ion exchange resin particles may be cohered with a polyvinyl alcohol polymer composition, for example, simply by dissolving a polyvinyl alcohol in water, mixing the resulting solution with diisocyanate as the crosslinking agent, intimately mixing the resulting mixture with the ion exchange resin particles to cause the particles to adhere to one another and solidify and drying the resulting cementitious composite. Thereafter, the dry mass may be crushed to obtain a desired grain size. Acrylic polymer compositions may be used to cohere ion-exchange resin particles by mixing a polyacrylate emulsion with ion-exchange resin particles to cause the particles to adhere to one another and solidify, and drying the resulting cementitious composite. Thereafter, the dry mass may be crushed to obtain the desired grain size. In either case, the ion-exchange grains resulting from the crushing are segregated, as by screening, to collect the grains having an effective diameter in the desired range, preferably from about 2 to about 50 mm. Alternatively, cementitious ion exchange resin grains having the preferred effective diameter, can be preformed, as by vigorously agitating the composite mixture during the cohering step.

U.S. Pat. No. 3,965,039 relates to the preparation of a catalyst by mixing a copolymer of styrene with divinylbenzene or diisopropenyl benzene and a thermoplastic material and moulding the obtained mixture by extrusion with heating to the melting temperature of the thermoplastic material so as to form moulded elements which are then treated first with a sulphonating agent and then with water.

U.S. Pat. No. 5,244,929 relates to shaped or moulded ion exchange resin bodies which it is said may be produced by block polymerisation of monomer mixtures in appropriate gravity moulds, although it is said that extruders or injection moulding machines may also be used as well as other apparatuses for forming polymerization mixtures in the process of hardening. Gel-like resins are also said to be suitable for forming the moulded bodies. It is said that the resins can be processed in suitable apparatuses to form the desired packing bodies and that it is also possible to perform forming operations on incompletely hardened resins which are still formable, to produce the packing bodies, wherewith suitable conditions are imposed after the forming to bring about final hardening. The use of an inert pore-former such as alkanes is said to enable the desired macroporous structure to be achieved.

There remains a need for an improved process for preparing a moulded ion exchange resin structure.

Accordingly, the present invention provides a process for preparing a moulded ion exchange resin structure characterised in that ion exchange resin precursor particles having chemically reactive functional groups on their surfaces are compressed into a preform having a predetermined shape, are subsequently chemically bonded together by a reaction of the functional groups present on their surfaces and are converted to an ion exchange resin.

The preform may be prepared by moulding ion exchange resin precursor particles in a die under an applied pressure of up to 2 tons, for example, by using a hydraulic press. Alternatively, the ion exchange resin precursor particles may be extruded into the predetermined shape.

Suitably the ion exchange resin precursor is a polystyrene-based ion exchange resin precursor prepared by co-polymerising styrene, divinyl benzene and a functionalised monomer having chemically reactive functional groups. Preferably, the ion exchange resin precursor is prepared by emulsion polymerisation. Preferably, the functionalised monomer is added towards the end of the polymerisation reaction so as to minimise the number of functional groups trapped within the ion exchange resin precursor particles and maximise the number of functional groups on the surface of the ion exchange resin precursor particles. Suitable functionalised monomers include N-hydroxymethylacrylamide, vinyl phenol, dicyclopentenyl methacrylate, hydroxymethylated diacetone acrylamide, allyl N-methylolcarbamate, N-formyl-N'-acryloyl methylenediamine, 2-acetoacetoxyethyl methacrylate, 2-cyanoacetoxyethyl methyacrylate, N-(2-acetoacetoxyethyl) acrylamide, and N-(2-acetoacetamidoethyl)methacrylamide.

Preferably, the functionalised monomer is N-hydroxymethylacrylamide in which case the functional groups present on the surface of the ion exchange resin precursor particles are chemically bonded together by means of a condensation reaction. Most preferably, the condensation reaction is acid catalysed. Suitable strong acid catalysts include sulphuric acid and hydrochloric acid.

The ion exchange resin precursor is preferably converted to a strong acid cation exchange resin, for example, having —$SO_3^-$ functional groups, in which case the condensation reaction which bonds the particles together is preferably catalysed by sulphuric acid which also acts as a sulphonating agent for the cation exchange resin precursor particles. Suitably, after compressing the ion exchange resin precursor particles into a preform having a predetermined shape, the preform is placed in contact with an acid catalyst for the chemical bonding step until the moulded resin structure no longer swells when placed in contact with a solvent, for example, acetone. Swelling of the moulded resin structure is evidenced by cracks on the surface of the moulded resin structure.

The condensation reaction may be performed at ambient or at elevated temperature, suitably 20°–80° C. Preferably, the temperature is increased from ambient temperature as the condensation reaction proceeds. The time taken to chemically bond the ion exchange resin precursor particles together is dependent on such factors as the size and shape of the preform and the condensation reaction temperature. Furthermore, where the functional groups are bonded by means of an acid catalysed condensation reaction the extent of bonding depends on the degree of penetration of the acid into the preform. When vinyl phenol is used as the functionalised monomer chemical bonding of the surface phenol groups may be achieved on addition of formaldehyde:

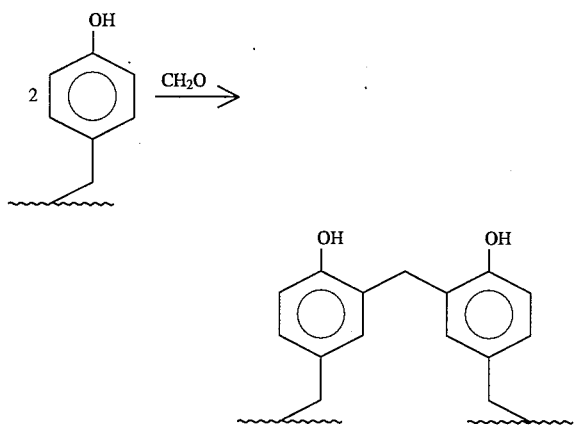

The extent of bonding depends on the degree of penetration of formaldehyde into the preform. Where the functionalised monomer is dicyclopentenyl methacrylate chemical bonding of the surface functional groups may be induced by thermal curing.

In a further embodiment of the present invention there is provided a moulded ion exchange resin precursor structure comprising particles of an ion exchange resin precursor which have been compressed into a preform having a predetermined shape and have been chemically bonded through the reaction of functional groups present on the surface of the particles.

The chemically bonded preform may subseqently be converted to an ion exchange resin structure by introduction of ion exchange groups, for example by sulphonation to introduce —$SO_3^-$ groups. Alternatively, the preform may be chemically bonded and convened to an ion exchange resin structure in a single step in the presence of, for example, sulphuric acid which acts as both a catalyst for the condensation reaction and as a sulphonating agent.

Thus, according to another embodiment of the present invention there is provided a moulded ion exchange resin structure prepared by the process as hereindescribed.

The ion exchange resin structure may be used as a catalyst in a reactive distillation process. A suitable reactive distillation process is a process for the esterification of an alcohol with an acid to produce an ester thereof.

According to another embodiment of the present invention there is provided a reactive distillation process which comprises contacting reactants in a distillation zone with a moulded ion exchange resin structure comprising particles of ion exchange resin precursor which have been compressed into a preform having a predetermined shape and have been chemically bonded through the reaction of functional groups present on the surface of the particles and converted to a catalytically active ion exchange resin.

Preferably, the reactive distillation process is an esterification process which comprises contacting an alcohol with an acid in a distillation zone in the presence of the moulded ion exchange resin catalyst structure.

The alcohol may be any suitable alcohol, for example, having 1 to 20 carbon atoms, saturated or unsaturated, mono- or polyhydric. Most preferably the alcohol is methanol. The acid may be any suitable acid, for example, an organic acid having 1 to 20 carbon atoms, saturated or unsaturated, mono- or polyfunctional. Most preferably the acid is acetic acid. The ion exchange resin is preferably a strong acid functionalised styrene divinyl benzene ion exchange resin, most preferably a sulphonated styrene divinyl benzene ion exchange resin. The esterification process of the present invention is preferably performed in a distillation zone. The predetermined shape of the preform is such that the catalyst structure may be packed into the distillation zone without causing severe pressure drops.

The temperature at which the distillation zone is operated is dependent upon the boiling point of the ester formed in the esterification process. The pressure in the distillation zone is adjusted to maintain the temperature within suitable limits. For example, when methanol is contacted with acetic acid the distillation zone may be operated at atmospheric pressure with head and base temperatures at the boiling points of the methyl acetate product (56°–57° C.) and water by-product (100° C.) respectively. Suitably, ester product is removed from the top of the distillation zone and water may be removed by azeotropic distillation from any convenient point in the column. The azeotroping agent may be the ester product or other suitable azeotroping agent.

The preparation of the moulded ion exchange resin structure will now be further illustrated by reference to the following Examples.

EXAMPLES

Preparation of Ion Exchange Resin Precursor Particles

Water (50 ml), styrene (50 ml), divinylbenzene (5 ml), potassium persulphate (0.5 g), Triton x-405 (TM) (ex Rohm and Haas; p-t-octylphenoxypolyethoxyethanol, 70% solution) (5.0 g), sodium dihydrogen phosphate (0.5 g) and sodium lauryl sulphate (0.1 g) were introduced to a 500 ml flat bottomed split flask which was equipped with an overhead stirrer. The contents of the flask were heated using an oil bath to a temperature of 65° C., with stirring, under an atmosphere of nitrogen. To the resulting stirred suspension was slowly added, over a period of 0.5 hour, approximately 5 ml of a solution of sodium metabisulphite (0.6 g) in 10 ml of water. Triton x-405 (5.0 g), water (50 ml), 48% hydroxymethylacrylamide solution in water (10 ml), styrene (50 ml), divinylbenzene (5 ml) and acrylic acid were then charged to a dropping funnel, together with the remainder of the sodium metabisulphite solution. The contents of the funnel were added dropwise to the flask and the contents of the flask were then stirred for a further 5 hours. The resulting white semi-solid was poured into a beaker containing methanol (500 ml), and the suspension thus formed was left to stir overnight for 18 hours. The white solid was filtered off from the methanol and was left to airdry for 24 hours. The dry white solid was then passed through a mill (1 mm screen).

Moulding of ion Exchange Resin Precursor Particles Into a Preform

A small hand assembled 3/16 inch diameter, 5/8 inch high die was assembled in an electrically driven laboratory hydraulic press. The die was filled with dried ion exchange resin precursor particles prepared according to the above procedure and the resin particles were compressed until an applied pressure of one ton was reached. The pressure was immediately released and an approximately 1/8 inch long preform pellet was removed from the die.

Sulphonation and Chemical Bonding of Ion Exchange Resin Precursor Preform

Example 1

12 preform pellets prepared according to the above procedure were placed in a 25 ml vial containing 98% concentrated sulphuric acid (20 ml). The sulphuric acid acts as both catalyst for the chemical bonding of the precursor particles of the preform and as a sulphonating agent. One pellet was removed from the sulphuric acid every 24 hours and was washed well with water (5×20 ml portions) until the washing water was no longer acidic, and was then left to stand in water overnight to remove any residual sulphuric acid. The washed and dried pellets were then placed in acetone for 5 days. The pellets removed after 24 and 48 hours respectively were light brown in colour and after being contacted with acetone displayed many cracks and rings owing to acetone penetration into the pellet. The pellets removed after 72 and 96 hours respectively both had two surface cracks after being placed in contact with acetone indicating that the central cores of the pellets had swollen as a result of acetone penetration into the pellets i.e. the central core of the pellet was not yet cross-linked. When a pellet removed after 168 hours was placed in contact with acetone no cracks were observed in the external surface of the pellet indicating that no swelling of the centre core had occurred i.e. the sulphuric acid had penetrated to the centre of the pellet which was now cross-linked. Pellets made in this way may be used for reactive distillation processes.

Comparative Example A

A preform ion exchange resin precursor pellet of ion exchange resin which had not been subject to the chemical bonding step was immersed in acetone (10 ml). The pellet immediately fell apart into a fine powder.

We claim:

1. A process for preparing a moulded ion exchange resin structure in which particles of an ion exchange resin precursor having chemically reactive functional groups on their surfaces are compressed into a preform having a predetermined shape, are subsequently chemically bonded together by a reaction of the functional groups present on their surfaces and are converted to an ion exchange resin.

2. A process as claimed in claim 1 in which said ion exchange resin precursor is prepared by co-polymerising styrene, divinyl benzene and a functionalised monomer selected from the group consisting of N-hydroxymethylacrylamide, vinyl phenol, dicyclopentenyl methacrylate, hydroxymethylated diacetone acrylamide, allyl N-methylolcarbamate, N-formyl-N'-acryloyl methylenediamine, 2-acetoacetoxyethyl methacrylate, 2-cyanoacetoxyethyl methyacrylate, N-(2-acetoacetoxyethyl) acrylamide, and N-(2-acetoacetamidoethyl)methacrylamide.

3. A process as claimed in claim 2 in which the ion exchange resin precursor is prepared by emulsion polymerisation.

4. A process as claimed in claim 3 in which the functionalised monomer is added towards the end of the polymerisation reaction.

5. A process as claimed in claim 1 in which said ion exchange resin precursor particles are chemically bonded together by a condensation reaction.

6. A process as claimed in claim 5 in which said condensation reaction is acid catalysed.

7. A process as claimed in claim 6 in which said acid catalysed condensation reaction is catalysed by sulphuric acid.

8. A process as claimed in claim 7 in which said ion exchange resin precursor particles are chemically bonded and converted to an ion exchange resin in a single step.

9. A process for preparing a moulded ion exchange resin precursor structure which comprises compressing particles of an ion exchange resin precursor having chemically reactive functional groups on their surfaces into a preform having a predetermined shape and subsequently chemically bonding the particles together by reaction of the functional groups present on their surfaces.

* * * * *